United States Patent
Ribadeau-Dumas

(10) Patent No.: US 8,563,049 B2
(45) Date of Patent: Oct. 22, 2013

(54) CONFECTIONERY CONTAINING ALGAE FOR THE PREVENTION OF ORO-DENTAL INFECTIONS

(75) Inventor: Guillaume Ribadeau-Dumas, Verlinghem (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 12/990,507

(22) PCT Filed: May 11, 2009

(86) PCT No.: PCT/FR2009/050858
§ 371 (c)(1),
(2), (4) Date: Nov. 1, 2010

(87) PCT Pub. No.: WO2009/147340
PCT Pub. Date: Dec. 10, 2009

(65) Prior Publication Data
US 2011/0044915 A1 Feb. 24, 2011

(30) Foreign Application Priority Data

May 14, 2008 (FR) ...................................... 08 53128

(51) Int. Cl.
*A01N 35/00* (2006.01)
(52) U.S. Cl.
USPC ....................................................... 424/725
(58) Field of Classification Search
None
See application file for complete search history.

(56) References Cited

U.S. PATENT DOCUMENTS

| | | | |
|---|---|---|---|
| 6,197,303 B1 | 3/2001 | Gedouin et al. | |
| 6,235,318 B1 * | 5/2001 | Lombardy et al. | 426/3 |
| 6,989,150 B1 | 1/2006 | Golz-Berner et al. | |
| 2002/0132000 A1 | 9/2002 | Saniez et al. | |
| 2004/0081665 A1 | 4/2004 | Kralovec | |
| 2005/0266018 A1 | 12/2005 | Boreyko | |
| 2007/0110684 A1 | 5/2007 | Jensen et al. | |
| 2007/0110799 A1 | 5/2007 | Leferve et al. | |
| 2008/0124286 A1 * | 5/2008 | Lisson | 424/61 |

FOREIGN PATENT DOCUMENTS

| | | | |
|---|---|---|---|
| CN | 1473510 A | | 2/2004 |
| CN | 1860902 | * | 11/2006 |
| EP | 1222860 A2 | | 7/2002 |
| FR | 2747922 | | 4/1996 |
| HU | 44 432 A | | 3/1988 |
| JP | 09028356 A | | 2/1997 |
| JP | 09048715 A | | 2/1997 |
| JP | 2004240604 A | | 9/2001 |
| JP | 2004123578 A | | 4/2004 |
| KR | 2001054258 | * | 7/2001 |
| KR | 20030020767 | | 3/2003 |
| KR | 718490 | * | 5/2007 |
| SU | 1528495 A | | 12/1989 |
| WO | WO 00/62762 A1 | | 10/2000 |
| WO | WO 0126617 A1 | | 4/2001 |
| WO | WO 2005060944 A1 | | 7/2005 |

OTHER PUBLICATIONS

Chlorella factor, 2 pages, 2010.*
Sun Chlorella USA, 2 pages, 2012.*
Translation of Chinese Office Action, dated Sep. 5, 2011, Application No. 200980117496.8.
French Search Report in connection with FR 0853128 mailed Jan. 16, 2009.

* cited by examiner

*Primary Examiner* — Michael Meller
(74) *Attorney, Agent, or Firm* — Young & Thompson

(57) ABSTRACT

The present invention relates in general to a sweet. More specifically, the present invention relates to a sweet which provides beneficial effects on the teeth. The sweet according to the present invention promotes good oro-dental hygiene, and more particularly provides oro-dental care, and promotes and maintains healthy teeth and gums. It is characterized in that it contains microalgae and/or extracts of microalgae, and more particularly *Chlorella* and/or extracts of *Chlorella*. Finally, the present invention also relates to the use of a sweet, preferably a sugar-free sweet, containing *Chlorella* for promoting and maintaining good oro-dental health.

10 Claims, No Drawings

CONFECTIONERY CONTAINING ALGAE FOR THE PREVENTION OF ORO-DENTAL INFECTIONS

FIELD OF THE INVENTION

The present invention relates in general to a confectionery. More specifically, the present invention relates to a confectionery that aims to provide dental benefits. The confectionery according to the present invention promotes good oral-dental hygiene, and more particularly promotes and maintains healthy teeth and gums. It is characterized in that it contains microalgae and/or extracts of microalgae, and more particularly *chlorella* and/or extracts of *chlorella*.

TECHNOLOGICAL BACKGROUND

Algae are among the first organisms that appeared on Earth, and are defined as eukaryotic organisms that lack roots, stems and leaves, but that have chlorophyll and also other pigments that are incidental to oxygen-producing photosynthesis. They are blue, red, yellow, golden and brown or else green. They represent more than 90% of marine plants and 18% of the vegetable kingdom, with their 40 000 to 45 000 species. Algae are organisms that are extremely varied both in their size and their shape and in their cellular structure. They live in an aquatic or very wet environment. They contain numerous vitamins and trace elements and are real concentrates of active agents that are stimulating and beneficial for health and beauty. They have anti-inflammatory, moisturizing, demulcent, regenerating, firming and antiaging properties. They also have "technological" features which make it possible to provide texture to a food product. Indeed, the famous additives E400 to E407 are in fact compounds extracted from algae, the thickening, gelling, emulsifying and stabilizing properties of which are used.

Microalgae, in the strict sense, are microscopic algae. Either unicellular or multicellular, they are photosynthetic microorganisms divided into two polyphyletic groups: eukaryotes and prokaryotes. Living in highly aqueous media, they may have flagellar motility.

*Chlorella* is a freshwater microscopic unicellular alga that appeared on Earth more than three billion years ago. It was discovered in 1890 by a Dutch microbiologist Martinus Beijernick, who was fascinated by its chlorophyll content and by the presence of an element giving it a high multiplication rate: the CGF (chlorella growth factor). *Chlorella* has the highest concentration of chlorophyll of all plants and its capacity for photosynthesis is considerable. Since its discovery, *Chlorella* has continued to generate considerable interest worldwide and today it is produced on a large scale for uses in nutritional and food supplements. Indeed *Chlorella* contains more than 60% of proteins which contain many amino acids essential for human and animal well-being. Chlorella also contains a lot of vitamins (A, beta-carotene, B1: thiamine, B2: riboflavin, B3: niacin, B5: pantothenic acid, B6: pyridoxine, B9: folic acid, B12: cobalamin, vitamin C: ascorbic acid, vitamin E: tocopherol, vitamin K: phylloquinone), lutein (family of carotenoids, powerful antioxidant), and minerals including calcium, iron, phosphorus, manganese, potassium, copper and zinc. Moreover, *chlorella* contains certain omega-type polyunsaturated fatty acids essential for good cardiac and cerebral functions and for preventing numerous diseases such as cancer, diabetes or obesity. *Chlorella* has three elements that participate in its action:

- the chlorophyll which is present in *Chlorella* at more than 4% (by weight) and is known for its purifying action.
- the cell membrane: not digested by the human digestive tract which lacks the enzymes necessary for the degradation of cellulose, it fixes heavy metals and toxins and accelerates the elimination thereof by natural routes.
- the CFG present at a level of 5% (by weight) is a powerful strengthening agent for the metabolism and for cell growth. It is an invaluable element originating from the nucleus of the cell and essentially containing amino acids, beta-glucans and nucleic acids. It gives *chlorella* a very rapid cell growth, multiplication and division rate.

The benefits related to the consumption of *chlorella* are very numerous. It is a food supplement used daily in Japan by 4 million people. To such an extent that the Japanese government has classified it as a "food of national interest". This precious alga is mainly, but not solely, recommended for:
- calming the nervous system and promoting sleep;
- reducing constipation, normalizing transit even in paralyzed people. It also restores the intestinal flora;
- stimulating the immune system;
- promoting acid-base balance;
- stimulating cell regeneration and slowing down ageing;
- decreasing the fats in the blood and reducing the risk of cardiovascular diseases;
- reducing hypertension;
- fixing heavy metals and other toxins, and eliminating them without damaging the liver; and
- healing and allaying stomach ulcers.

Document US 2004/0081665 describes the use of *chlorella* extracts containing high molecular weight polysaccharides and polysaccharide complexes possessing immunomodulating activity, which are intended to increase the production of cytokines and are used as components in the preparation of vaccines.

Document KR20030020767 describes a pharmaceutical preparation, possibly in the form of a tablet, a capsule or granules, for the prevention and treatment of osteoporosis, characterized in that it contains *chlorella* as active principle.

Document FR2747922 describes the use of concentrated extracts of *chlorella*-type algae for elaborating a product intended for preventing and treating skin diseases, characterized in that said extracts protect the Langerhans cells of the epidermis from ultraviolet radiation.

In the present invention, the word alga is used independently of the size of the algae, therefore including microalgae also. Preferably, they are microalgae.

No relevant document has been identified by the Applicant concerning the use of algae and/or extracts of algae in the prevention of oral-dental infections or diseases and/or for the upkeep of good oral-dental hygiene.

The best-known and most recognized method for maintaining good dental hygiene is regular brushing of the teeth and daily use of dental floss. However, these methods do not make it possible to prevent gingival inflammations and periodontal infections due to problems of inaccessibility of certain parts of the teeth or of the gums during brushing. Moreover, some people do not wish or do not have the opportunity to brush their teeth correctly and/or regularly. For example, certain situations may prevent an individual from maintaining good dental hygiene, such as illness or hospitalization. Other situations render brushing of the teeth difficult or impossible: inconvenience of locations, lack of hygiene, embarrassment, etc. In order to encourage oral-dental health, tests have been carried out in order to deliver active principles or medicines within the oral cavity, such as antiseptics, zinc salts, antibiotics, oxidants, folic acid, coenzyme Q10, etc.

Document WO 00/62762 describes sugar-free chewing gums with a therapeutic effect comprising a gum base, a soluble portion, a flavor, calcium carbonate and a food-grade acid, intended for remineralizing dental enamel and for preventing and treating dental caries.

Document US 2007/0110684 describes a method for treating and preventing dental problems through the use of an effective amount of *Morinda citrifola*, an Indian tree extract. The extracts of this plant may be in the form of a powder, a tablet, a chewing gum, granules, a toothpaste, a lotion for mouthwashes, in combination with other additives and/or active principles.

However, the effectiveness, the absorption, the metabolism, the bioavailability, the secondary effects, the regulation and the costs associated with these medicaments and/or active principles delivered into the oral cavity are some of the problems which it is necessary to overcome today.

Based on this observation, the Applicant has had the merit of discovering, surprisingly and unexpectedly, that the combination of the properties of a confectionery, and more particularly of a sugar-free confectionery, with that of microalgae and/or extracts of microalgae, and more particularly *chlorella*, made it possible to obtain a non-cariogenic confectionery having a beneficial effect for oral-dental health. Indeed this confectionery, and more particularly this sugar-free confectionery, combined with *chlorella*, provides a technically and economically viable solution to the prevention of oral-dental infections or diseases and/or to the upkeep of good oral-dental hygiene, enables simple use, under all circumstances and therefore promotes the maintenance of a healthy mouth throughout the day. Moreover, the use of a confectionery as a vector for *Chlorella* makes it possible to deliver the *Chlorella* directly to the site of oral infections and thus enables an optimization of the treatment, unlike the *chlorella*-containing supplements that currently exist and which must be swallowed directly. Indeed, it is difficult to imagine that the extracts of *Chlorella* contained in these supplements can have a beneficial action on oral-dental hygiene once they have reached the stomach. Furthermore, these supplements are not recognized or prescribed for the prevention of oral-dental infections or diseases and/or the upkeep of good oral-dental hygiene.

Moreover, the use of a confectionery as a vector enables simple use, at any moment of the day, with no particular constraint. The use of other means enabling good oral-dental health to be maintained, i.e. brushing the teeth and/or the use of mouthwashes after meals, specifically have the major disadvantage of not being able to be carried out simply, regularly and each time that the need therefore is felt.

SUMMARY OF THE INVENTION

The present invention therefore relates to a confectionery, and more particularly a sugar-free confectionery, containing microalgae and/or extracts of microalgae, intended for the prevention of oral-dental infections or diseases and/or for the upkeep of good oral-dental hygiene, consequently enabling good oral-dental health to be maintained. The present invention relates more particularly to sugar-free confectionery containing *chlorellas* and extracts of *chlorellas*. Finally, the present invention also relates to the use of a confectionery, preferably a sugar-free confectionery, containing *Chlorella* in order to promote and maintain good oral-dental hygiene and good oral-dental health.

DETAILED DESCRIPTION OF THE INVENTION

In the present invention, the expression "oral-dental health" should be understood to mean the absence of chronic oral or facial pain, of oral lesions, of periodontopathy (infection affecting the gums), of dental caries and of periodontolysis, and also other pathologies and disorders affecting the mouth and the oral cavity.

In the present invention, the expression "oral-dental infections or diseases" denotes dental caries, aphthae, halitosis, gingivitis, periodontal diseases, and all other oral lesions.

Dental caries is a transmissible infectious disease, which is the result of acid erosion generated by dental plaque bacteria. Every day, generally after meals, bacterial plaque forms rapidly on the teeth and constitutes a thin and sticky matrix, also known as a biofilm, on the surface of the enamel of the teeth and on the gums. This matrix encompasses food debris and bacteria which develop owing to the sugars contained in foods and drinks. The acids produced by the bacteria cause a demineralization of the enamel that covers the teeth. This demineralization constitutes the starting point for dental caries, it is stage 1 for which there is no sensitivity. Stage 2 is the attack on the dentin (substance forming the inner layer of the tooth), recognizable by a sensitivity to external stimuli such as heat, cold, sugar. Stage 3 is characterized by such a destruction of the hard tissues that there is attack on the dental pulp that can be characterized by spontaneous pains (raging toothache). Finally, stage 4 is pulp death or spontaneous devitalization with bacterial proliferation in the canals and around the tooth. This is the most serious stage leading to a tooth infection or abscess.

This infection source represents a danger for general health. The bacteria may migrate into the organism by the bloodstream and graft to organs such as the heart, the kidneys, the joints, etc. Dental caries constitutes an evolving process and there may not be spontaneous recovery.

Oral-pharyngeal aphthae and aphthoses occupy an important place among lesions of the oral mucous membrane. Their occurrence may be linked to nutritional, psychological (especially stress) or hygiene factors. They are superficial mucosal ulcers. Their development takes place in four phases. The prodromal stage is marked by the appearance of burning or stinging sensations followed, during the pre-ulcerous phase by the appearance of an erythematous macula centered on a yellow spot. Thus macula, by necrotizing, will give way to a larger or smaller ulcer depending on the clinical form characterizing the acme phase. The healing phase leads to recovery with or without sequelae depending on the size of the lesion. When oral aphthae are not isolated and are accompanied by other symptoms, they may be the sign of Behçet's disease or of inflammatory diseases of the intestine such as ulcerative colitis or Crohn's disease. The treatment should be adapted to the degree of severity of the disease and it begins with the elimination of local promoting factors, that is to say by elimination of tartar and by good oral hygiene. Sporadic forms respond to symptomatic local treatments. More severe forms require a systemic treatment, the efficacy of which has been controlled. The ideal treatment should act on the pain, on the lesions themselves and if possible prevent subsequent attacks.

The causes of mouth odor, also known as halitosis, are most often found in the oral cavity. Hydrogen sulfide and methyl mercaptan are the main foul-smelling components that originate from the bacterial degradation of protein substrates containing thiol groups and disulfides which are primary derivatives of the cellular elements in saliva. The content of sulfur-containing volatile compounds in the breath is particularly high in the case of an inflammatory condition or after long periods of reduction of the salivary flow, during sleep and after cessation of oral cleansing. This content of sulfur-containing volatile compounds in the breath may significantly be reduced in most cases by means of meticulous brushing of the oral cavity, including the dorso-posterior surface of the tongue or by rinsing with a mouthwash containing zinc salts. The tongue is very often the cause of halitosis. This is because it comprises numerous villosities which retain the bacteria responsible for bad breath which form a deposit on the tongue.

Gingivitis or gum disease is described as a bacterial infection of the gums, or inflammation of the gums at the initial stage. It appears by bleeding of the gums, but without reaching the bone which supports the teeth. It may be treated by rigorous hygiene treatment at home including mouthwashes with a disinfecting solution, dental cleaning including scaling to remove dental plaque and tartar. If it is untreated, it may lead to tooth loss. Gingivitis is the first stage of periodontitis, which is a more aggressive form of the disease that is described by bleeding of the gums, destruction of the bone and of the tissues supporting the tooth, teeth which move slightly or severely, bad breath and periodontal pockets (deep space between a tooth and the gum). It may be treated by curettage and surfacing which is a non-surgical deep cleaning and scaling procedure, by open curettage which is a surgical procedure requiring the gum to be opened before carrying out the curettage, then closure of the gum using suture stitches and dressings. The most advanced stages will be treated with bone grafts or gum grafts.

The present invention relates to a confectionery, and preferably to a sugar-free confectionery to be consumed within the oral cavity, containing microalgae and/or extracts of microalgae for the prevention of oral-dental infections or diseases, some examples of which have been explained in detail above, and therefore for the upkeep and maintenance of good oral-dental hygiene.

According to one preferred mode, said microalgae and/or extracts of microalgae are present in an amount of 0.2 to 65% by weight, preferably 0.2 to 50% by weight, preferably 1 to 40% by weight, preferably 1 to 30% by weight, and more preferably 5 to 28% by weight or 10 to 28% by weight.

According to one preferred mode, the microalgae and/or the extracts of microalgae are chosen from the group constituted by *Chlorella*, *Spirulina* and *Odontella*.

According to one even more preferred mode, the microalgae and/or the extracts of microalgae of the present invention are derived from the *Chlorella* genus, and preferably from *Chlorella vulgaris*, *Chlorella pyrenoidosa*, *Chlorella regularis*, *Chlorella sorokiniana*, and more preferably from *Chlorella vulgaris*.

According to another preferred mode, the confectioneries according to the present invention contain extracts of microalgae, and preferably extracts of CGF.

According to one variant of the present invention, the *Chlorella* microalgae and/or the extracts thereof may be combined with other algae and/or extracts of algae that also have a beneficial effect on well-being in general.

Examples of such algae and/or extracts of algae are, for example, DHA or docosahexaenoic acid, fatty acids from the group of omega-3 fatty acids component, in particular of the nerve cells, contained in the oceanic algae of the genera *Schizochytrium, Iridaea, Porphyra* and more particularly *Porphyra yezoensis, Gymnogongrus* and more particularly *Gymnogongrus crenulatus* and *Gymnogongrus griffithsiae, Crypthecodinium* and more particularly *Crypthecodinium cohnii, Hypnea* and more particularly *Hypnea musciformis, Meristotheca* and more particularly *Meristotheca senegalensis* and *Meristotheca papulosa*. Other examples of combinations with *Chlorella* and/or extracts of *Chlorella* are algae of the genera *Spirulina, Pheophyceae, Rhodophyceae, Chlorophyceae* and/or extracts of lutein, zeaxanthin, xanthophyll, laminarin and chlorophyll.

The term "confectionery" (synonyms: sweets, sweetmeats, candies, etc.) refers, in the present invention, to any flavored food product having a sweet taste, the consistency of which may be hard or soft, which may be coated with chocolate and which is consumed by sucking and/or by chewing within the oral cavity.

According to one preferred mode, the confectioneries of the present invention are all the confectioneries of the following types: boiled sugars (more commonly known as hard boiled candies), dragees, jelly candies, gums, caramels, toffees and fudges, chewing gums, bubble gums, chewy pastes, tablets and lozenges.

According to another preferred mode, the confectioneries of the present invention may be aerated confectioneries such as, for example, marshmallows.

According to another preferred mode, the confectioneries of the present invention are prepared with chocolate, in any form, which may be: bars, candies, bonbons, truffles, lentils, etc.

According to one variant of the invention, the confectioneries of the present invention may be film-coated. Film-coating consists in applying a film-forming liquid composition which becomes, after drying, a protective film. This film-coating serves, for example, to protect the active principles contained in the confectionery, to protect the confectionery itself from moisture, from shocks, from friability, and also to confer the confectionery attractive visual properties: shine, uniform color, smooth surface, etc.

According to one more preferred variant, the compositions used for the film-coating are those described in patent application WO 2005/060944, of which the Applicant is the proprietor.

According to another preferred mode, the confectioneries of the present invention may also, when it is possible, be filled with liquid, pasty, solid, powdered, etc. fillings. They may also be coated with chocolate, sugar-coated, candied, glazed, etc.

According to another more preferred mode, the confectioneries of the present invention are sugar-free confectioneries.

According to another even more preferred mode, the confectioneries of the present invention are sugar-free confectioneries, prepared from polyols, from a mixture of polyols, from a mixture of polyols and soluble fibers, from mixtures of polyols, soluble fibers and proteins, and are particularly suitable for the present invention due to their innocuousness towards teeth and due to their reduced calorie content compared to sucrose.

An example of a particularly advantageous combination is the use of NUTRIOSE®, which is a complete range of soluble fibers recognized for their benefits, and manufactured and sold by the Applicant. NUTRIOSE® is a partially hydrolyzed wheat and maize starch derivative which contains up to 85% fiber. This high fiber content makes it possible to increase the digestive tolerance, to improve calorie control, to extend energy release and to obtain a lower sugar content. Furthermore, NUTRIOSE® is one of the best tolerated fibers available on the market. It shows a higher digestive tolerance, allowing better incorporation than other fibers, which represents real dietary advantages.

The tendency toward healthier food continues to gain ground and modifies modes of consumption and purchasing habits significantly. Consuming less sugar while continuing to indulge oneself is the desire of more and more consumers in response to the many nutritional recommendations.

Furthermore, sugar-free products are particularly advantageous for the manufacture of confectioneries which have a therapeutic function, for example confectioneries for coughs or airways, chewing gums containing calcium that contribute to oral-dental hygiene, etc.

According to one even more preferred mode of the present invention, said confectionery is a sugar-free polyols based chewing gum which may be or not coated and/or film-coated by one of the methods known and described in the prior art.

Without being limited to one particular mechanism, the consumption of a chewing gum containing *chlorella* and/or extracts of *Chlorella* is capable of contributing to the upkeep of good dental hygiene, by preventing, inter alia, the formation of dental plaque, which is responsible for many oral-dental infections or diseases. The mastication of said chewing gum promotes the activation of saliva defense mechanisms, thus preventing bacterial growth on the surface of the teeth. The combined action of the *Chlorella* contained in the chewing gum further reinforces these antibacterial defense mechanisms.

This beneficial effect is also found when the *chlorella* is included in a confectionery to be sucked or to be chewed. Again, the production of saliva is promoted, and this makes it possible to considerably reduce the growth of bacteria on the teeth.

According to one even more preferred mode of the present invention, flavors such as mint, and fruit flavors may be added in order to promote a greater salivary secretion, and thus reinforce the protective action. Other flavors such as, for example, menthol, eucalyptol, thymol, methyl salicylate, liquorice and cinnamaldehyde may, due to their inherent antibacterial property, reinforce the action of destroying undesirable germs of the oral cavity.

According to another preferred mode of the present invention, active principles may be added to the confectionery. The expression "active principle" is understood, within the present invention, to mean any active molecule that has a proven pharmacological effect and a therapeutic advantage that is also clinically proven.

According to another preferred mode of the present invention, a sugar-free chewing gum containing *chlorella* and/or extracts of *Chlorella* may be consumed at any time in order to prevent oral-dental infections or diseases and to allow the upkeep of good oral-dental hygiene and consequently the maintenance of good oral-dental health.

The confectioneries according to the invention may be administered to individuals having an oral infection. In particular, they are particularly suitable for individuals suffering from lack of oral-dental hygiene, by choice or by necessity. It is also appreciated that the confectioneries of the present invention may be used quite simply as a complement to good oral-dental hygiene.

According to one preferred mode, one particularly suitable confectionery may be a confectionery with a rough texture such as that described by the Applicant in patent EP 1 222 860, that, by itself, makes it possible to combat the problems of halitosis. Such confectioneries with a rough texture may also be tablets, lozenges, etc. The combined action of both *chlorella* and rough texture of the confectionery reinforces the beneficial action as regards maintaining a healthy mouth.

According to another preferred mode of the present invention, the amount of confectionery consumed per day and per individual lies between 0.5 g and 50 grams. According to one even more preferred mode, the amount consumed per day lies between 2 g and 30 grams.

In the particular case where the confectionery is a chewing gum or a chewy paste, the amount of confectionery consumed per day is less than 15 grams and preferably around 10 grams.

According to one preferred mode of the present invention, the effective dose or amount of *chlorella* and/or of extract of *Chlorella* consumed per day lies between 0.1 g and 10 g.

According to one more preferred mode, the effective dose or amount of *Chlorella* and/or of extract of *chlorella* consumed per day lies between 1 g and 3 g.

According to one even more preferred mode, the effective dose or amount of *Chlorella* and/or of extract of *Chlorella* consumed per day is 2 grams.

The confectioneries of the present invention are consumed at any opportune moment and for the desired time.

According to one preferred mode, the confectioneries are consumed after each ingestion of liquid and/or of food, such as for example after meals, moments where bacterial attacks and formation of dental plaque are the most frequent.

According to one preferred mode of the present invention, the confectioneries are consumed at least twice a day, and preferably at least three times a day.

According to one preferred mode of the present invention, two tablets of chewing gum are chewed together.

According to another preferred mode, two tablets are sucked together, and preferably three.

According to another preferred mode, the confectioneries remain present in the oral cavity for at least 2 minutes, preferably for at least 5 minutes and more preferably still for at least 10 minutes.

The invention will be better understood with the aid of the following examples which are meant to be illustrative but not limiting.

EXAMPLE 1

Sugar-Free Chewing Gums Containing Polyols and *Chlorella*

A. Formulation for Manufacture of the Centers (Ingredients Expressed as Percentage by Weight)

| | |
|---|---|
| Gum base | 35.0% |
| (e.g.: Optima from Cafosa Gum SA Barcelona (Spain)) | |
| Maltitol Maltisorb ® P35 | 36.3% |
| LYCASIN ® 80/55 maltitol syrup (75% DS) | 7.0% |
| *Chlorella* (powder, 96% DS) | 20.0% |
| Liquid mint flavoring | 1.5% |
| (e.g.: Ref. SN748096, IFF Company) | |
| Aspartame | 0.2% |

B. Method (for 60 kg of Centers)
  Loading procedure (in minutes) into a Z-blade kneader at 50° C.
  0 min: introduction into the kneader of the melted gum base (heated overnight at 50° C.) and of half of the Maltisorb® P35
  4 min: addition of the *Chlorella* and of the aspartame
  8 min: addition of the other half of the Maltisorb® P35
  10 min: addition of the LYCASIN® 80/55 maltitol syrup
  12 min: addition of the liquid mint flavoring
  14 min: unloading of the kneader (gum at around 53° C.) and division of this gum into loaves of around 2 kilograms. Storage of these loaves for around 1 h in air at 20° C. and 50% relative humidity. The temperature of the loaves of gum is around 43° C. when they arrive at the extruder.

Extrusion (Togum TO-E82 machine)

Temperature of the body of the extruder: 41° C.

Temperature of the head of the extruder: 44° C.

Lamination: 4 pairs of rollers—scoring: 2 pairs of rollers (Togum TO-W191 machine)

The strips of gum obtained are dusted with a mixture containing 50% by weight of talc and 50% by weight of Mannitol 60.

Storage: the strips of unseparated centers are stored for around 48 h in air at 15° C. and 50% relative humidity, before being coated.

C. Coating of the Centers Obtained Above

Composition of the coating syrup (70% DS-75° C.)

|  | Ingredients by weight | Composition as DS |
|---|---|---|
| MALTISORB ® P200 maltitol | 25.00 kg | 93.25% |
| Solution of gum arabic (40% DS) | 3.35 kg | 5.00% |
| TiO$_2$ | 0.27 kg | 1.00% |
| Chlorella | 0.20 kg | 0.75% |
| Water | 9.48 kg |  |
|  |  | 100.0% |

Composition of the coating layer (%)

| MALTISORB ® P200 maltitol | 90.54% |
|---|---|
| Solution of gum arabic (40% DS) | 4.85% |
| TiO$_2$ | 0.97% |
| Liquid mint flavoring | 0.97% |
| Chlorella | 0.73% |
| Water | 1.94% |

Composition of the chewing gum with *chlorella*

|  | % | per unit g |
|---|---|---|
| MALTISORB ® maltitol | 55.82 | 1.0184 |
| Gum base | 22.40 | 0.4087 |
| Gum arabic | 1.75 | 0.0319 |
| Mint flavoring | 1.31 | 0.0239 |
| LYCASIN ® 80/55 (dry) | 3.36 | 0.0613 |
| TiO$_2$ | 0.35 | 0.0064 |
| Chlorella | 13.06 | 0.2383 |
| Water | 1.82 | 0.0332 |
| Sweetener | 0.13 | 0.0024 |

The above chewing gums containing *Chlorella* in the gum and in the peripheral coating layer were tasted by a panel of tasters, and their taste was judged to be satisfactory and rather pleasant.

EXAMPLE 2

Confectionery Having a Rough Texture Containing *Chlorella*

According to one preferred mode, one particularly suitable confectionery could be a confectionery with a rough texture such as that described by the Applicant in patent EP 1 222 860.

A. Formulation (Ingredients Expressed as Percentage by Weight)

| NEOSORB ® P60W sorbitol | 39.00% |
|---|---|
| Maltisorb ® P200 maltitol | 39.00% |
| Chlorella (powder, 96% DS) | 20.00% |
| Liquid mint flavoring (e.g.: Ref. SN748096, IFF Company) | 1.00% |
| Magnesium stearate | 1.00% |

B. Preparation of the Powder

Mixing of the sorbitol and of the maltitol

Spraying the liquid flavoring onto the preceding powdery mixture

Addition of the *chlorella*

Addition of lubricant

Mixing until homogenization

C. Compression

Compression on a desktop alternating press equipped with flat and round punches having a diameter of 18 mm.

D. Characteristics of the Tablets Obtained

Weight per tablet: 1.76 g

Thickness: 5 mm

Dose of *Chlorella* per tablet: 352 mg

Hardness measured on the Erweka TBH 30 machine: 110 N

The rough confectioneries were tasted by a panel of tasters, and their taste was judged to be satisfactory and rather pleasant.

EXAMPLE 3

Recipes for Chewy Pastes Containing *Chlorella*

A. Formulation for the Two Tests

|  | Ingredients by weight (g) | |
|---|---|---|
|  | Test 1 | Test 2 |
| LYCASIN ® HBC maltitol syrup (73% DS) | 584 | 710 |
| Mannitol 60 | 126 | 0 |
| Vegetable fat* | 40 | 40 |
| Glycerol monostearate | 3 | 3 |
| 125 bloom gelatin (solution containing 40% DS) | 17 | 17 |
| Chlorella (96% DS) | 230 | 230 |
| Apple flavoring** | 0 | qs (1.5 ml) |
| Total | 1000 g | 1000 g |
| Cooking temperature | 116° C. | 116° C. |
| aw (water activity) | 0.54 | 0.5 |

*Biscuitine 621 from Loders Croklaan
**Ref. SN748106 IFF Company

B. Method

Preparation of the solution of gelatin containing 40% of DS.

Cooking of the LYCASIN® HBC (and of the Mannitol 60, for test 1) at 116° C.

In a mixer, addition of the solution of gelatin and kneading.

Addition of the melted vegetable fat and of the emulsifier, and kneading.

Addition of the *Chlorella* and of the flavoring, and kneading.

Cooling, cutting and packing.

C. Composition of the Finished Products of the Two Tests

|  | Composition of the products (g) | |
|---|---|---|
|  | Test 1 | Test 2 |
| LYCASIN ® HBC (73% DS) | 46.6 | 59.1 |
| Mannitol 60 | 13.8 | 0.0 |
| Vegetable fat | 4.4 | 4.6 |
| Glycerol monostearate | 0.3 | 0.3 |
| Gelatin 125 bloom (40% solution) | 0.7 | 0.8 |
| *Chlorella* | 24.2 | 25.2 |
| Apple flavoring | qs | qs |
| Residual water | 10.0 | 10.0 |
| Total | 100.0 | 100.0 |

The apple-flavored chewy confectioneries were tasted by a panel of tasters, and their taste was judged to be satisfactory and rather pleasant.

EXAMPLE 4

Gelatin Jelly Candies Filled with *Chlorella*

A. Formulation (Ingredients Expressed as Percentage by Weight)

|  | Ingredients by weight (g) | |
|---|---|---|
|  | Preparation A | Preparation B |
| Sucrose | 311 | 105 |
| Glucose syrup (42 DE) (75% DS) | 408 | 231 |
| Gelatin (220 bloom) (40% DS) | 170 | / |
| Citric acid (50% DS) | 17 | 18 |
| Flavoring and colorant | qs | 17 |
| Water | 94 | 389 |
| CLEARAM ® CR2010 starch | / | 46 |
| *Chlorella* | / | 194 |
| Total | 1000 g | 1000 g |

B. Method
Preparation and cooking of the outer mass gelled with gelatin (Preparation A)
Place the gelatin in a bain-marie at 60° C.
Mix the sugar with the glucose syrup and water, and begin to heat the mixture.
Cook the preceding mixture at 110° C.-115° C.
Cool the mixture, and at 90° C. add the solution of gelatin, the citric acid and the flavoring and colorant. The Brix of the mixture is around 78%.
Preparation and cooking of the *Chlorella* filling (Preparation B)
Mix the sugar with the glucose syrup and the water, and begin to heat the mixture.
Disperse the CLEARAM® CR2010 starch in cold water, add the preparation to the preceding mixture and cook in order to gelatinize the whole mixture and obtain a transparent mass.
Disperse the *Chlorella* in water.
Add the solution of *Chlorella* to the previously obtained transparent mass.
Production of said confectionery
Deposit the gelled outer mass (preparation A) and the *Chlorella* filling (preparation B) into a casting machine comprising two casting hoppers for filled products.
Control the casting machine so that the finished product comprises 90% of the mass (preparation A) and 10% of filling (preparation B).
Deposit the filled confectioneries in dry molding starch and leave for 24 hours.
Remove them and brush them before oiling them.

C. Composition of the Finished Product

|  | Composition of the products in % |
|---|---|
| Sucrose | 34.45 |
| Glucose syrup (42 DE) (75% DS) | 34.73 |
| Gelatin (220 bloom) (40% DS) | 7.20 |
| Citric acid (50% DS) | 1.08 |
| Flavoring and colorant | qs |
| Residual water | 20.10 |
| CLEARAM ® CR2010 starch | 0.5 |
| *Chlorella* | 1.94 |
| Total | 100% |

The gelatin jelly candies filled with *Chlorella* were tasted by a panel of tasters, and their taste was judged to be satisfactory and pleasant.

EXAMPLE 5

Tablets Containing *Chlorella*

A. Formulation (Ingredients Expressed as Percentage by Weight)

| LYCATAB ® C | 37.25% |
|---|---|
| *Chlorella* (powder, 96% DS) | 62.50% |
| Magnesium stearate | 0.25% |

B. Preparation of the Powder
Mix the three ingredients together by hand for 5 minutes.
C. Compression
Compression on a FETTE P 1000 rotary press equipped with concave round punches having a diameter of 16 mm and a radius of curvature of 25 mm.
D. Characteristics of the Tablets Obtained
Weight per tablet: 1000 mg
Thickness: 5.76 mm
Dose of *Chlorella* per tablet: 625 mg
Hardness measured on the Erweka TBH 30 machine: 40 N
The tablets containing *Chlorella* were tasted by a panel of tasters, and their taste was judged to be satisfactory and rather pleasant.

EXAMPLE 6

Tablets Containing *Chlorella* and NUTRIOSE®

A. Formulation (Ingredients Expressed as Percentage by Weight)

| NUTRIOSE ® FB06 | 49.75% |
|---|---|
| *Chlorella* (powder, 96% DS) | 49.75% |
| Magnesium stearate | 0.50% |

B. Preparation of the Powder
Mix the three ingredients together.

C. Compression

Compression on a FETTE P 1000 rotary press equipped with concave round punches having a diameter of 16 mm and a radius of curvature of 25 mm.

E. Characteristics of the Tablets Obtained

Weight per tablet: 1000 mg
Thickness: 5.75 mm
Dose of *Chlorella* per tablet: 497 mg
Hardness measured on the Erweka TBH 30 machine: 40 N The tablets containing *Chlorella* in combination with NUTRIOSE® were tasted by a panel of tasters, and their taste was judged to be satisfactory and rather pleasant.

EXAMPLE 7

Effect of the Consumption of Confectioneries Containing *Chlorella* on the Reduction of Dental Plaque An internal study was carried out in order to measure the efficacy of the consumption of the confectioneries described in Example 2 of the present application, on the reduction of the formation of dental plaque, the source of many oral-dental infections or diseases.

Dental plaque is defined as a heterogeneous accumulation that adheres to the surface of the teeth or that is lodged in the gingival-dental space, composed of a microbial community rich in aerobic and anaerobic bacteria which are coated in an intercellular matrix of microbial and salivary origin. It is a yellowish white gel that is drab, persistent and similar to adhesive. The varied microbial community, located at the surface of the tooth develops where food residues remain by using them for their metabolism. Dental plaque unbalances the oral ecosystem and allows oral pathologies to take hold. It is responsible for dental caries attack. It is also considered the starting point for periodontal disease (gingivitis, periodontitis). It may also play a role in halitosis.

Experimental Protocol 15 volunteers were chosen, among which were:
  8 women aged between 20 and 55 years old;
  7 men aged between 20 and 55 years old;
including:
  5 smokers;
  10 people who consume at least 3 coffees or teas per day.

These volunteers do not suffer from any particular dental problem and have good oral-dental hygiene: brushing their teeth twice a day (morning and evening). The test consisted in measuring the dental plaque 1 hour after having lunch, owing to a dental plaque colored revelator. This revelator is in the form of a liquid or of tablets, and is available in drugstores. The product contains erythrocin which colors the dental plaque on the teeth in fuchsia pink, and thus makes it possible to reveal it in order to be able to visually quantify it.

The quantification of the dental plaque was carried out visually by assessing the colored dental surface relative to the total dental surface.

For the first ten days, the volunteers did not consume the confectioneries of the present invention, and did not follow any food or tobacco restriction. Their dental plaque was revealed 1 hour after the end of having lunch.

Then, over the following ten days, the volunteers consumed two rough tablets described in Example 2, allowing them to melt while making them circulate in the oral cavity for at least 5 minutes, half an hour after having had their lunch. Then, one hour after the end of their lunch, i.e. around 20 minutes after the complete melting of the confectioneries, their plaque was revealed under the same conditions, using a liquid colored revelator. Again, the volunteers did not follow a food or tobacco restriction.

Results of the Measurements

When volunteers did not consume the confectioneries of the present invention, the dental plaque revealed 1 h after the end of lunch was evaluated for 13 of the 15 volunteers as representing more than 60% of the total visible dental surface. For the remaining two volunteers, the dental plaque formed 1 h after the end of lunch was evaluated visually as representing 40% of the total visible dental surface.

When the volunteers consumed the confectioneries of the present invention according to the experimental protocol, the dental plaque revealed was evaluated as representing only 20% of the total visible dental surface, for 12 of the 15 volunteers.

The dental plaque of the 3 remaining volunteers was evaluated as representing 30% of the total visible dental surface.

This example demonstrates that the regular consumption of the confectioneries of the present invention enables a significant reduction of the formation of dental plaque, and therefore participates in maintaining good oral-dental hygiene. Furthermore, the consumption of the confectioneries according to the invention makes it possible to replace brushing of the teeth after lunch, which is often ruled out for reasons of ease or inconvenience.

The invention claimed is:

1. A confectionery selected from the group consisting of candies, gums, caramels, toffees, fudges, marshmallows, and chocolate consisting essentially of a polyol and 5 to 40 wt % of a microalgae selected from the group consisting of *Chlorella* and *Odontella* in the total confectionery.

2. The confectionery as claimed in claim 1, wherein the microalgae is 5 to 28 wt % in the total confectionery.

3. The confectionery as claimed in claim 1, wherein the confectionery is sugar-free.

4. The confectionery as claimed in claim 1, wherein the microalgae is selected from the group consisting of *Chlorella vulgaris*, *Chlorella pyrenoidosa*, *Chlorella regularis*, and *Chlorella sorokiniana*.

5. The confectionery as claimed in claim 1, wherein the confectionery is a candy selected from the group consisting of boiled sugars, dragees, jelly candies, and lozenges.

6. The confectionery as claimed in claim 1, wherein the confectionery is filled with a liquid, pasty, solid and/or powdered filling.

7. The confectionery as claimed in claim 1, wherein the microalgae is 20 to 40 wt % in the total confectionery.

8. The confectionery as claimed in claim 1, wherein the confectionery is a gum selected from the group consisting of chewing gums and bubble gums.

9. The confectionery as claimed in claim 1, wherein the confectionery is in a form of tablet.

10. A confectionery selected from the group consisting of candies, gums, caramels, toffees, fudges, marshmallows, and chocolate consisting essentially of a polyol and 1 to 40 wt % of a microalgae selected from the group consisting of *Chlorella* and *Odontella* in the total confectionery, wherein the confectionery is sugar-free.

* * * * *